US009782435B2

(12) United States Patent
Kjellin et al.

(10) Patent No.: US 9,782,435 B2
(45) Date of Patent: Oct. 10, 2017

(54) PRODUCTION OF MOLDABLE BONE SUBSTITUTE

(71) Applicant: Promimic AB, Gothenburg (SE)

(72) Inventors: Per Kjellin, Gothenburg (SE); Paul Handa, Gothenburg (SE)

(73) Assignee: Promimic AB, Gothenburg (SE)

( * ) Notice: Subject to any disclaimer, the term of this patent is extended or adjusted under 35 U.S.C. 154(b) by 47 days.

(21) Appl. No.: 14/737,741

(22) Filed: Jun. 12, 2015

(65) Prior Publication Data

US 2015/0352258 A1 Dec. 10, 2015

Related U.S. Application Data

(60) Continuation of application No. 13/936,585, filed on Jul. 8, 2013, now Pat. No. 9,066,935, which is a
(Continued)

(51) Int. Cl.
*A61K 33/42* (2006.01)
*A61L 27/50* (2006.01)
(Continued)

(52) U.S. Cl.
CPC .............. *A61K 33/42* (2013.01); *A61L 27/28* (2013.01); *A61L 27/46* (2013.01); *A61L 27/502* (2013.01);
(Continued)

(58) Field of Classification Search
None
See application file for complete search history.

(56) References Cited

U.S. PATENT DOCUMENTS 5,681,873 A * 10/1997 Norton .................. A61F 2/2846
424/426
5,904,718 A * 5/1999 Jefferies .................... A61F 2/28
128/898
(Continued)

FOREIGN PATENT DOCUMENTS

SE 520688 8/2003
WO WO 01/76649 A1 10/2001
(Continued)

OTHER PUBLICATIONS

De Groot et al. "A novel method for fabrication of biodegradable scaffolds with high compression moduli" *Journal of Materials Science* 8:707-712 (1997).
(Continued)

*Primary Examiner* — Robert A Wax
*Assistant Examiner* — Thor Nielsen
(74) *Attorney, Agent, or Firm* — Myers Bigel, P.A.

(57) ABSTRACT

Composites and methods of producing a mouldable bone substitute are described. A scaffold for bone growth comprises nanocrystalline hydroxyapatite (HA), a bioresorbable plasticizer, and a biodegradable polymer. Plasticizers of the invention include oleic acid, tocopherol, eugenol, 1,2,3-triacetoxypropane, monoolein, and octyl-beta-D-glucopyranoside. Polymers of the invention include poly(caprolactone), poly(D,L-Lactic acid), and poly(glycolide-co lactide). Methods of regulating porosity, hardening speed, and shapeability are also described. Composites and methods are described using nanocrystalline HA produced with and without amino acids. The scaffold for bone growth described herein displays increased strength and shapeability.

23 Claims, 14 Drawing Sheets

Related U.S. Application Data division of application No. 12/660,876, filed on Mar. 5, 2010, now abandoned.

(60) Provisional application No. 61/209,385, filed on Mar. 6, 2009.

(51) Int. Cl.
*A61L 27/54* (2006.01)
*A61L 27/28* (2006.01)
*A61L 27/46* (2006.01)
*A61L 27/58* (2006.01)

(52) U.S. Cl.
CPC ............... *A61L 27/54* (2013.01); *A61L 27/58* (2013.01); *A61L 2400/12* (2013.01); *A61L 2430/02* (2013.01)

(56) References Cited

U.S. PATENT DOCUMENTS

| | | |
|---|---|---|
| 5,990,381 A | 11/1999 | Nishihara |
| 6,013,591 A | 1/2000 | Ying et al. |
| 6,165,486 A | 12/2000 | Marra et al. |
| 6,299,902 B1 | 10/2001 | Jun et al. |
| 6,311,690 B1 | 11/2001 | Jefferies |
| 6,331,312 B1 | 12/2001 | Lee et al. |
| 7,004,974 B1 | 2/2006 | Larsson et al. |
| 7,186,759 B2 | 3/2007 | Seppala et al. |
| 2003/0135284 A1 | 7/2003 | Crouch et al. |
| 2003/0180344 A1* | 9/2003 | Wise ............ A61L 27/443 424/423 |
| 2005/0031704 A1 | 2/2005 | Ahn |
| 2006/0013857 A1 | 1/2006 | Kronenthal |
| 2006/0257448 A1 | 11/2006 | Weber |
| 2008/0220233 A1* | 9/2008 | Kjellin ............ B82Y 30/00 428/220 |
| 2009/0048145 A1* | 2/2009 | Hellerbrand ......... A61L 27/446 514/1.1 |
| 2011/0212406 A1 | 9/2011 | Jensen |

FOREIGN PATENT DOCUMENTS

| WO | WO 2007/015208 A2 | 2/2007 |
|---|---|---|
| WO | WO 2008/000488 A1 | 1/2008 |

OTHER PUBLICATIONS

Guo et al. "Fabrication of nanostructured hydroxyapatite and analysis of human osteoblastic cellular response" *Journal of Biomedical Materials Research Part A* 82A:1022-1032 (2007).

Meirelles et al. "Nano hydroxyapatite structures influence early bone formation" *Journal of Biomedical Materials Research Part A* 87A:299-307 (2008).

Sun et al. "Fabrication of hydroxyapatite-poly(ε-caprolactone) scaffolds by a combination of the extrusion and bi-axial lamination process" *Journal of Materials Science* 18:1017-1023 (2007).

Tanaka et al. "Improvement in Thermal Stability and Temperature Dependence of Diffractivity in Low-$T_g$ Photorefractive Polymers Dispersed with Plasticizers" *Japanese Journal of Applied Physics* 43(9A):6097-6100 (2004).

The Merck Index "Oleic Acid" www.knovel.com 3 pages (2006).

* cited by examiner

PRODUCTION OF MOLDABLE BONE SUBSTITUTE

CROSS-REFERENCE TO RELATED APPLICATIONS

This application claims priority from U.S. Provisional Application Ser. No. 61/209,385 filed Mar. 6, 2009.

FIELD OF THE INVENTION

The present invention relates generally to a composite, serving as a scaffold for bone cell growth, comprised of nanocrystalline hydroxyapatite ("HA"), a plasticizer and a biodegradable polymer. Certain embodiments of the invention, not intending to be limiting, are disclosed. In one embodiment of the invention a method is provided for controlling the hardening speed of the composite by addition of specific biodegradable plasticizers resulting in a composite with a prolonged shapeability time and a high final strength.

BACKGROUND OF THE INVENTION

In medicine, there are many situations where it is necessary to aid the human body to build new bone. Physical trauma, such as fractures, may damage the bone tissue in such complex ways, which makes standard bone fracture treatments insufficient. Tumours, which destroy large portions of bone tissue, can make it impossible for the body to heal the injury by itself. Another example is so called sinus lifts, where the natural bone is too thin to support a dental implant and the bone tissue has to be augmented.

The insertion of a bone scaffold is a common way of solving these issues. Bone scaffold materials contain a structure and composition, which will trigger the formation of bone when implanted in the human body, and act as a cultivating substrate for bone cells. Some bone scaffolds are also able to withstand the mechanical loads, which was excerted on the original bone tissue. Natural bone consists of rod-shaped calcium phosphate crystals with a length of 20-40 nm, 2 nm thick and 2-4 nm wide, surrounded by a collagen network[1]. HA, with the chemical formula $Ca_5(PO_4)_3OH$, is a mineral, which closely resembles the calcium phosphate mineral found in natural bone.

Synthetic bone scaffolds can be in the form of a powder, such as HA or tricalcium phosphate. Powder based products are successful in restoring bone tissue, but are less suitable for load-bearing applications. There are also injectable, hardening bone scaffold materials, which aim to ease the insertion procedure. One example is a mixture of HA and calcium sulfate hemihydrate, this composition is mixed with water and injected into the desired area. The calcium sulfate reacts with water and serves as a "glue" between the HA crystals. The calcium sulfate crystals are subsequently resorbed by the body, resulting in a porous structure, which in turn creates a suitable environment for bone cell growth[2]. Another type of bone scaffold is the rigid type, these usually consist of porous HA or tricalcium phosphate, which has been sintered at high temperatures. Some commercial products use natural coral as a raw material. The coral is reacted with phosphate salts at high temperature, and the resulting structure is a rigid porous HA material[3]. Due to environmental concerns, synthetic methods to produce the porous HA structure are becoming more common. The primary advantages of rigid bone scaffold products are the non-shrinking structure of the material, and the porosity, which increases the available surface area for the bone cells to grow on. One disadvantage is the brittleness of the structure, due to the fact that the material contains no substances, such as polymers, which may dissipate forces applied to the material, as in natural bone. Another disadvantage is that the material requires careful fitting before it can be inserted in the body.

One way of decreasing the brittle nature of a rigid mineral scaffold is to incorporate a polymer into the structure. Polymer/mineral composite materials consist of a polymer, which can be biodegradable, and a mineral with bone regeneration properties, such as HA. The polymer makes the composite elastic and crack-resistant, while the mineral induces the formation of endogenous bone. The biodegradation speed can be governed by the choice of polymer. Biodegradable polymers include synthetic polyesters such as poly(caprolactone) (PCL), poly(lactide) or poly(lactic acid) (PLA) and poly(glycolide) (PGL), but also naturally occurring polymers, such as collagen, hyaluronic acid, chitin and chitosan. These polymers undergo hydrolysis in the human body, producing non-toxic degradation products[4]. PCL is a polyester with the composition $(C_6H_{10}O_2)_n$. It has a Tg of −60° C. and a melting temperature of 60° C. For biomaterial applications, it is used in sutures, root canal fillings and drug delivery applications. PCL exhibits a significant high degree of elongation until breakage (>700%), which makes it suitable in load-bearing applications[4]. Melting of PCL produces a paste with a viscosity, which increases with the molecular weight. A PCL melt with a molecular weight of 80000 g/mol is a viscous, sticky substance. Above the melting temperature, it can be casted to any desired shape. Upon cooling, the polymer rapidly becomes more viscous, since the polymer chains aggregate and become less mobile. Composites of PCL/HA are reported in the literature[5, 6] and have been shown to have good mechanical properties and also to induce bone cell growth. However, these composites are generally too stiff to be shaped at room temperature.

For making dense, non-porous polymer/mineral composites, the mixing is generally undertaken by melt extrusion[7, 8] or solvent/solution casting[8, 9]. Dense composites have high strengths but are lacking in osseointegration properties since the bone cells have less surface area to grow on. A porous structure is a better scaffold for bone cell growth. One method of making a porous structure is to add a so called porogen, i.e. a material, which supports the initial structure and is subsequently removed by washing or heating[10]. A common porogen is sodium chloride, which is readily removed with water[11-13] (U.S. Pat. No. 5,766,618) before the implantation.

In addition to the porosity of the bone scaffold, the crystal size of the calcium phosphate is also important to stimulate the growth of endogenous bone. For certain biomaterial applications, it is highly desirable to use nanosized HA, i.e. with a particle size of 1-100 nm in length. Other terms for particles in this size interval may be "nanocrystalline" or simply "nanoparticles". It is generally considered that the bioactivity of HA is improved if the HA crystals are of a similar size and shape as those produced by the human body. The body recognizes the nanosized HA as a part of its own bone tissue and starts to grow new bone around the foreign object. For implants, a coating with nanosized HA will significantly increase the bone cell activity compared to microsized HA[14, 15]. For polymer/HA composites, the bioactivity as well as the strength is greatly improved with nanosized HA[16, 17].

For many situations it is highly advantageous if the polymer/HA composite is shapeable or injectable at room temperature, or at temperatures that are close to the human body temperature. When implanted, and after hardening, the material should be able to withstand high mechanical loads, and preferably the material should be porous to enable the ingrowth of bone cells. The composite should also contain HA particles of the same size and shape as those found in the human body in order to stimulate the growth of endogenous bone.

In the literature, several patents describe products, which aim to solve the above needs. WO2007015208A describes an injectable bone scaffold comprising poly(vinyl alcohol), water and tricalcium phosphate, which upon mixing generates a hydrogel. Depending on the amount of polymer present, the composite can be readily injected in cavities in the time range of 2-60 minutes. The hardening is induced by leakage of water into the surrounding media. However, unlike the invention herein, this patent application employs a polymer, which is degraded very slowly in the human body. Furthermore, the composite comprises a non-porous and dense bone scaffold.

U.S. Pat. No. 6,331,312 describes a method of producing a bone scaffold material, consisting of poorly crystalline apatite together with biodegradable polymers. The product is mixed with water, which creates a mouldable composite. However, unlike the invention herein, this patent application describes preparation routes mainly intended for attaining non-porous and dense composites.

U.S. Pat. No. 7,004,974 describes a substance, which consists of calcium phosphate granules, lipid and hyaluronic acid. When mixed with water, this substance generates a mouldable and injectable composite, with relatively low compression strengths.

US2006013857 describes different compositions, which have the form of a putty at body temperature and which are hard at room temperature. The compositions contain gelatin, calcium stearate, tocopheryl acetate and in some examples microsized HA particles (6-12 μm). This document does not describe the use of nanosized HA, nor does it describe a method to control the hardening speed of the composite.

There are a few documents on the use of biodegradable polymers together with HA and plasticizers. U.S. Pat. No. 7,186,759 for example, describes a three component system consisting of a biocompatible polymer, a water-soluble or hydrolytically degrading polymer, such as poly(ethylene glycol) and a bioactive substance. The composite can be softened upon heating and hardened upon cooling. The bioactive substance may be a substance, which can induce bone growth, such as hydroxyapatite. Upon removal of the hydrolytically degradable component, for instance upon contact with water or other fluids present in the human body, a porous structure will be generated with the bioactive substance present in the pores, in the polymer matrix or at the outer surface of the composite material. However, even though patent U.S. Pat. No. 7,186,759 discloses a composite that contains a porogen in the form of a water-soluble or hydrolytically degrading polymer, the mouldability has proven to be restricted to a short period of time. It should also be noted that the degradation speed of PEG is in the same range as the degradation of the supporting polymer[18, 19] and the desired porosity of the composite upon removal of the PEG polymer will not be very efficient. Furthermore, the patent employs micrometer sized HA particles.

SE520688 reports on an injectable bone replacement material, which is composed of two parts. One part contains a biologically active substance, such as a biologically compatible oil. The second part comprises bone cement consisting of calcium sulphate (in order to accelerate the hardening process) and/or a bone mineral substitute, such as HA (in the size range of 10 μm, preferably smaller). Mixing the two components renders a bone replacement material, which is of low viscosity, enabling facile injection of the material into the area of choice. The material can either be injected to fill the void between an implant and the surrounding tissue or as a sole component. The bone replacement material can also be moulded into various shapes before being inserted into the body since the maximum hardness is reached after approximately 4 to 8 minutes depending on the composition. However, the invention does not employ biodegradable polymers as primary components.

WO2008/000488 describes a biomaterial for tissue regeneration, which may consist of a bioactive material, such as beta-tricalcium phosphate, a biodegradable polymer, such as poly(lactic-co-glycolic acid), and a water binding agent, such as calcium sulfate, to decrease the degradation of the biodegradable polymer. This document also describes the use of a compound, such as poly(ethylene glycol) 400, to improve the dissolution of the biodegradable polymer. This document does not describe the use of a plasticizer to prolong the shapeability of the composite, and does not describe the use of nanosized HA.

As previously mentioned, it is highly advantageous for a bone substitute to 1) be shapeable and injectable at room temperature or at a temperature not exceeding 37° C. for a long period of time, 2) be able to withstand high mechanical loads, 3) be porous to enable the ingrowth of bone cells and 4) contain HA particles of the same size and shape as those found in the human body in order to stimulate the growth of bone cells as efficiently as possible.

The method of combining the above mentioned approaches either simultaneously or in sequence for synthesizing a strong, mouldable composite, has not been previously disclosed.

SUMMARY OF THE INVENTION

A primary object of the present invention is to provide a composite, serving as a scaffold for bone cell growth, comprising of nanocrystalline HA, a plasticizer and a biodegradable polymer. Another object is to provide a method of controlling the hardening speed of the composite by addition of specific biodegradable plasticizers to provide a composite with a long shapeability time and a high final strength.

Other objects and advantages of the present invention will become obvious to the reader and it is intended that these objects and advantages are within the scope of the present invention.

DETAILED DESCRIPTION OF THE INVENTION AND PREFERRED EMBODIMENTS THEREOF

Reference will now be made in detail to the presently preferred embodiments of this invention.

The present invention comprises a composite of nanocrystalline HA, a plasticizer and a biodegradable polymer. The composite can be shaped to the desired form at room temperature. After a certain period of time, the composite hardens and will have a similar strength as a pure polymer-HA composite. The composite hardening speed is controlled by the addition of a biodegradable plasticizer. When implanted, the plasticizer is resorbed by the body and leaves a porous structure consisting of nanocrystalline HA and polymer. After the removal of the plasticizer, the mechanical strength of the composite will increase considerably. Due to the bioactive properties of the nanosized HA particles, this structure will serve as an excellent scaffold for bone cell growth.

The nanosized HA is synthesized with a method, which involves the mixing of an aqueous dispersion of a calcium compound with a phosphoric acid solution (see Example 1). The resulting HA crystals have a size of 10-20 nm in length, and a specific surface area of above 200 $m^2/g$. Another method of making nanosized HA involves the mixing of an aqueous dispersion of a calcium compound and amino acids, together with a solution of phosphoric acids and amino acids. A method of producing nanocrystalline HA with amino acids is described in U.S. Patent Publication No. 60/996,561, the disclosure of which is hereby incorporated by reference. A more specific, but not limited, example is created by mixing an aqueous dispersion of a calcium compound and L-aspartic acid, together with a solution of phosphoric acids and L-lysine (see Example 2). The synthesis may also be carried out with other amino acids.

When amino acids are present in a crystallizing solution, the amino acids attach to the surface of the growing calcium phosphate crystals and prevent agglomeration and crystal growth by electrostatic repulsion. The result is a suspension of nanosized HA particles with a size of 10-20 nm in length, coated with amino acids. The amino acids can be used to improve the strength of the composite, but also as anchors to attach other functional groups to the HA crystals, such as carboxylic acids, epoxides, cyanides, aldehydes, esters, alkyl halides, acid halides, acid anhydrides, ketones and phosphates. Optionally, the amino acids may be removed prior to the insertion of the crystals in the composite, by heating to 350° C. or by extensive washing with water.

Figure 1:
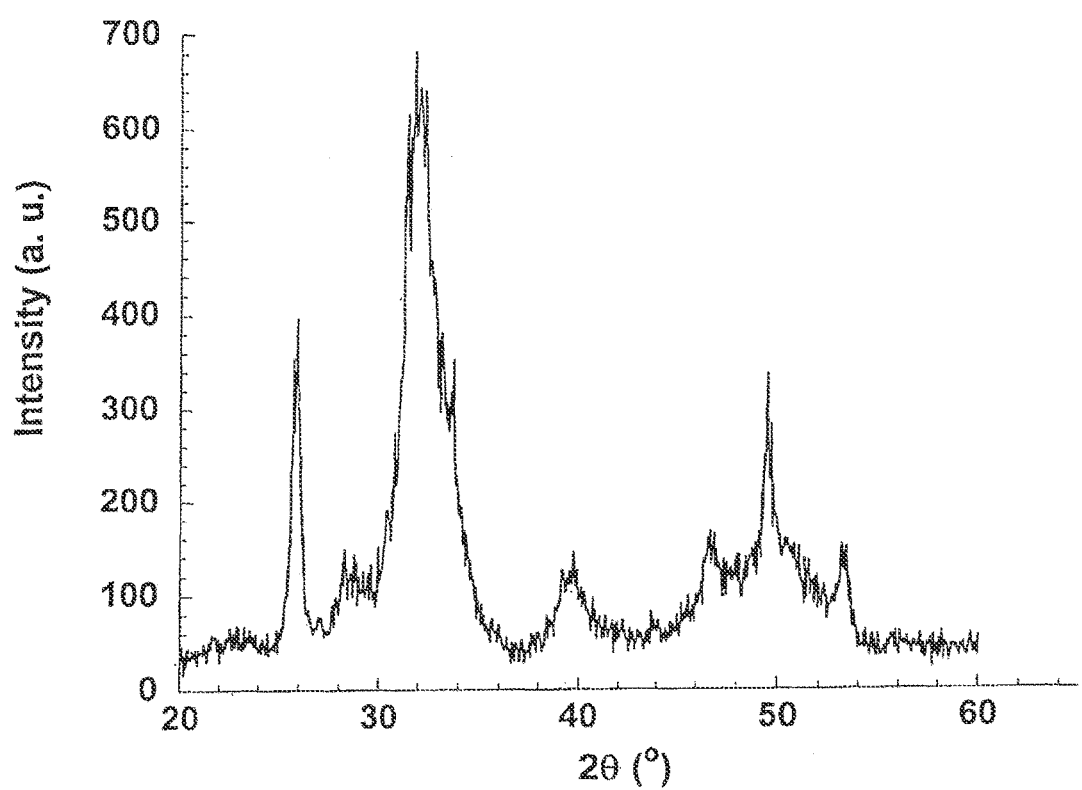
FIG. 1. XRD diffractogram of the nanosized HA particles, obtained with CuKα-radiation (1.54 Å).
Figure 2:
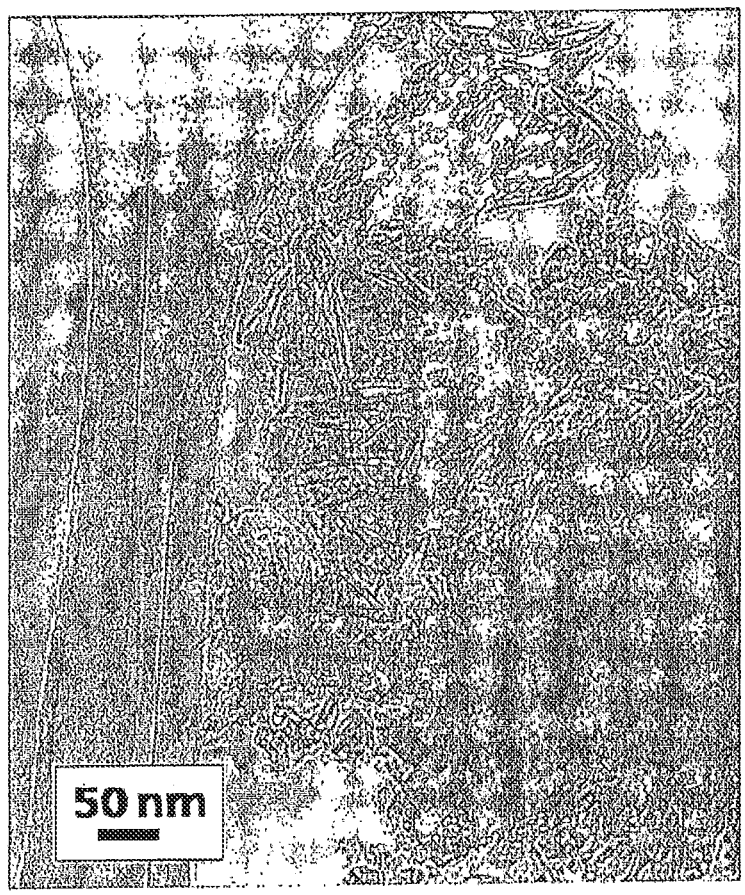
FIG. 2. TEM image of the nanosized HA particles (magnification 1001 k×).
Figure 3:
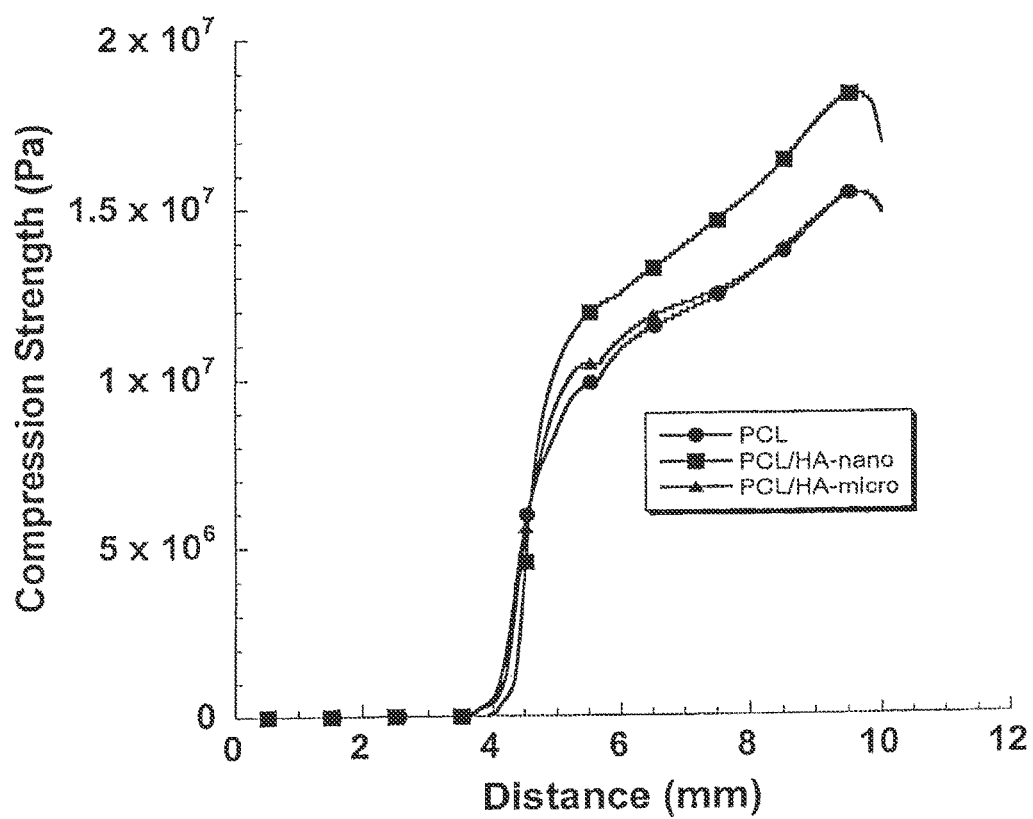
FIG. 3. Graph of compression strength (Pa) versus distance (mm) for pure PCL, PCL/nanosized HA and PCL/microsized HA composites at room temperature.

A powder X-ray diffractogram of the HA powder can be seen in FIG. 1. As the TEM image in FIG. 2 shows, the precipitated crystals are around 10-20 nm long (for preparation of TEM samples, see Example 14).

The plasticizers are fully or partially soluble in the polymer matrix. When the composite is heated, the viscosity decreases due to the increased mobility of the polymer chains. Upon cooling to room temperature, the composite retains its shapeability since the plasticizer prevents rapid aggregation of the polymer chains. After a certain period of time, typically 30 minutes, the polymer chains start to aggregate, leading to a rapid increase in viscosity and strength. Plasticizers, which have the ability to control the hardening process may include biodegradable lipophilic substances, such as oleic acid, tocopherol and eugenol, triglycerides, such as 1,2,3-triacetoxypropane (triacetin) but also amphiphilic substances, such as monoolein and octyl-beta-D-glucopyranoside.

Polymers that are suitable to use in combination with the nanocrystalline HA and the plasticizer include, but are not limited to, biodegradable polyesters, such as poly(caprolactone), poly(DL-lactic acid), and poly(glycolide-co-lactide). These polymers may also be used in combination.

In one embodiment, the composite comprises a mixture of nanocrystalline HA, PCL, and tocopherol. This composite is heated to 70° C. and allowed to cool to 37° C. or to room temperature. At 37° C., the composite can be shaped by hand for at least 60 minutes. At room temperature, the composite can be shaped by hand for at least 45 minutes.

In another embodiment, the composite comprises a mixture of nanocrystalline HA, PCL, eugenol, and tocopherol. After melting and cooling in room temperature, this composite can be shaped by hand for at least 120 minutes.

In yet another embodiment, the composite comprises a mixture of nanocrystalline HA, poly(D,L-lactide) and eugenol. After heating and cooling in room temperature, this composite is a viscous paste which does not harden after prolonged storage.

In yet another embodiment, the composite comprises a mixture of nanocrystalline HA, poly(D,L-lactide), tocopherol and eugenol. After heating and cooling in room temperature, this composite has an elastic, rubber-like appearance.

In yet another embodiment, the composite is a mixture of nanocrystalline HA, PCL, poly(D,L-lactide), eugenol and tocopherol. After heating and subsequent cooling in room temperature, this composite can be shaped by hand for approximately 30 minutes.

In yet another embodiment, the composite is a mixture of nanocrystalline HA, PCL, monoolein and 1,2,3 Triacetoxypropane. This composite has similar mechanical properties as the PCL/tocopherol/HA composite.

The advantage of including additional biologically active factors in the bone growth scaffold is apparent to the skilled artisan. Depending on the patient's medical needs, these factors may include, but are not limited to, antibiotics, chemotherapeutics, bone cell inducers, bone cell stimulators, tissue promoting factors, tissue decomposition inhibitors, and growth factors.

The possibility of replacing or mixing the nanocrystalline HA with other calcium phosphates is also apparent to the skilled artisan. Depending on the desired characteristics of the bone scaffold, these calcium phosphates may include, but are not limited to, tricalcium phosphate, octacalcium phosphate, tetracalcium phosphate and dicalcium phosphate.

The mechanical properties of the composite samples were studied by measuring the pressure (Pa) versus distance (mm) at various times (15, 20, 30, 45, 60, 120, 240, 360 and 1440 min) upon cooling after being heated to 70° C. for 1 hour, as can be seen in FIGS. 3-8. It should be noted, that FIGS. 3-8 only exhibit representative examples of the measurements in order to ease the purpose of reading. Each composite was molded into cylinders carrying the dimensions: 7 mm (height)×7 mm (diameter). The molding procedure was executed simply by filling a disposable syringe with composite followed by heating to between 70 and 100° C. for at least 1 h. The cylindrical shape was created by injecting the viscous mass into a teflon mold carrying the dimensions described above. The pressure exerted on the sample was recorded as a function of distance. The values in Tables 1-4 were recorded when the sample had been compressed from an original height of 7 mm to 1 mm. Experiments were performed on a TA-HDi Texture Analyzer (Stable Micro Systems) and employed a compression speed of 0.2 mm/s.

Compression Strength of PCL

As mentioned in the Background section, a melted sample of PCL which is cooled below its melting point will not solidify immediately. The polymer chains will gradually begin to aggregate, creating an increase in viscosity and compression strength. We found that a sample with a compression strength above 4 MPa was hard to shape by hand or to inject with a syringe. As shown in Table 1, for pure PCL this value is reached in less than 15 minutes after the polymer is allowed to cool in room temperature. It can also be seen that after roughly 30 minutes of cooling, PCL reached a maximum strength of 14.8 MPa (see FIG. 3).

Nanosized HA Versus Microsized HA

In the following sections, nanocrystallline HA prepared in the presence of amino acids will be referred to as nanosized HA, whereas nanocrystalline HA synthesized in absence of amino acids will be referred to as HA without amino acids.

A series of compression strength measurements were undertaken in order to compare the effect of nanosized HA to microsized HA. The microsized HA was obtained from Sigma Aldrich, Sweden. The results are shown in Table 1 and FIG. 3. With nanocrystalline HA, (29 wt % HA), the compression strength after 20 minutes was 15.6 MPa, which made the composite impossible to shape by hand after this period of time. The maximum strength was reached after 30 minutes of cooling and was around 17 MPa, thus 15% higher than for pure PCL. The commercially available, microsized HA gave a composite with similar mechanical properties as for pure PCL, with a compression strength of around 15 MPa after 30 min and onwards. Thus, using nanosized HA instead of microsized HA creates a composite with a 15% higher strength. The results also show that blending HA, either nanosized or microsized, with PCL has an effect on the hardening process, mainly on the initial stages, even though the final hardened state has a similar strength. HA accelerates the polymer aggregation process and significantly lowers the time, during which the material can be shaped by hand. The invention includes methods wherein the hardening speed of the composite is increased by adding more nanocrystalline HA.

Addition of Plasticizers

To prolong the time during which the PCL/HA composite could be shaped, a number of different biologically compatible plasticizers were evaluated. The results of these measurements are shown in FIGS. 4a-4c and Table 2.

Figure 4A:
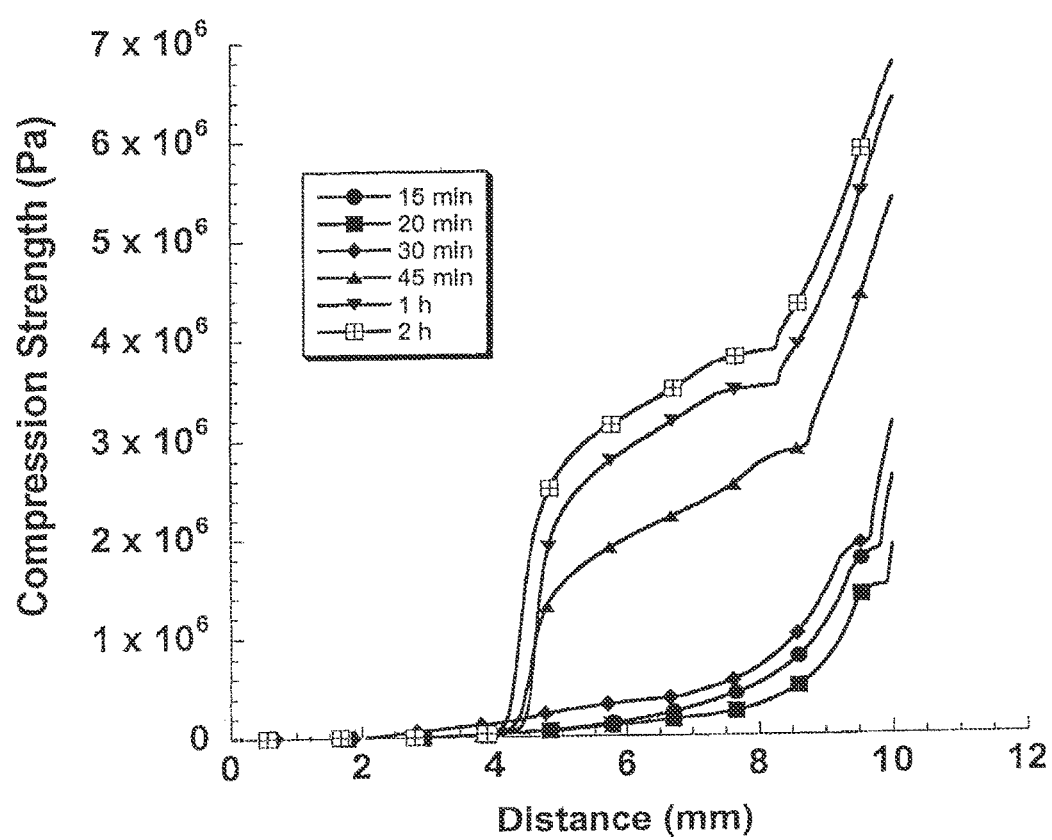
FIG. 4A. Compression strength (Pa) versus distance (mm) at various times and after being heated to 70° C. for 1 hour and then allowed to cool in room temperature for composites with PCL/tocopherol/nanosized HA with amino acids (29 wt % HA).
Figure 4B:
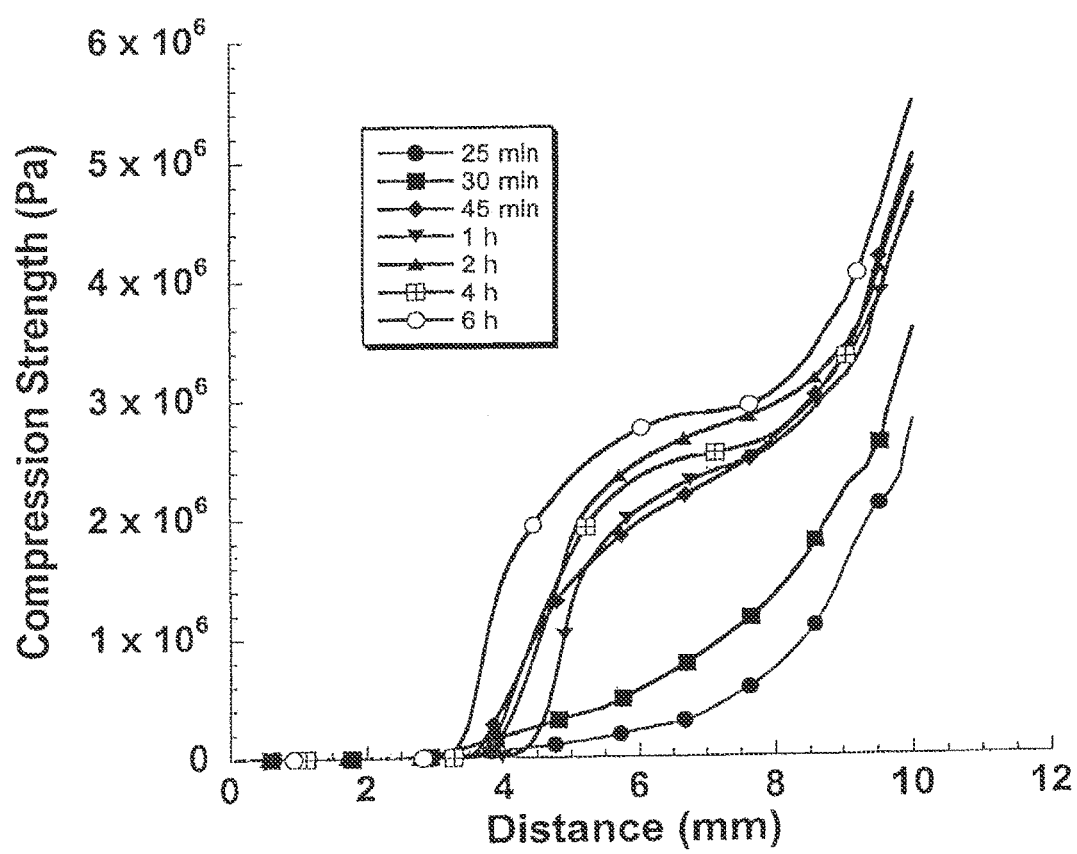
FIG. 4B. Compression strength (Pa) versus distance (mm) at various times and after being heated to 70° C. for 1 hour and then allowed to cool in room temperature for composites with PCL/tocopherol/nanosized HA without amino acids (29 wt % HA).
Figure 4C:
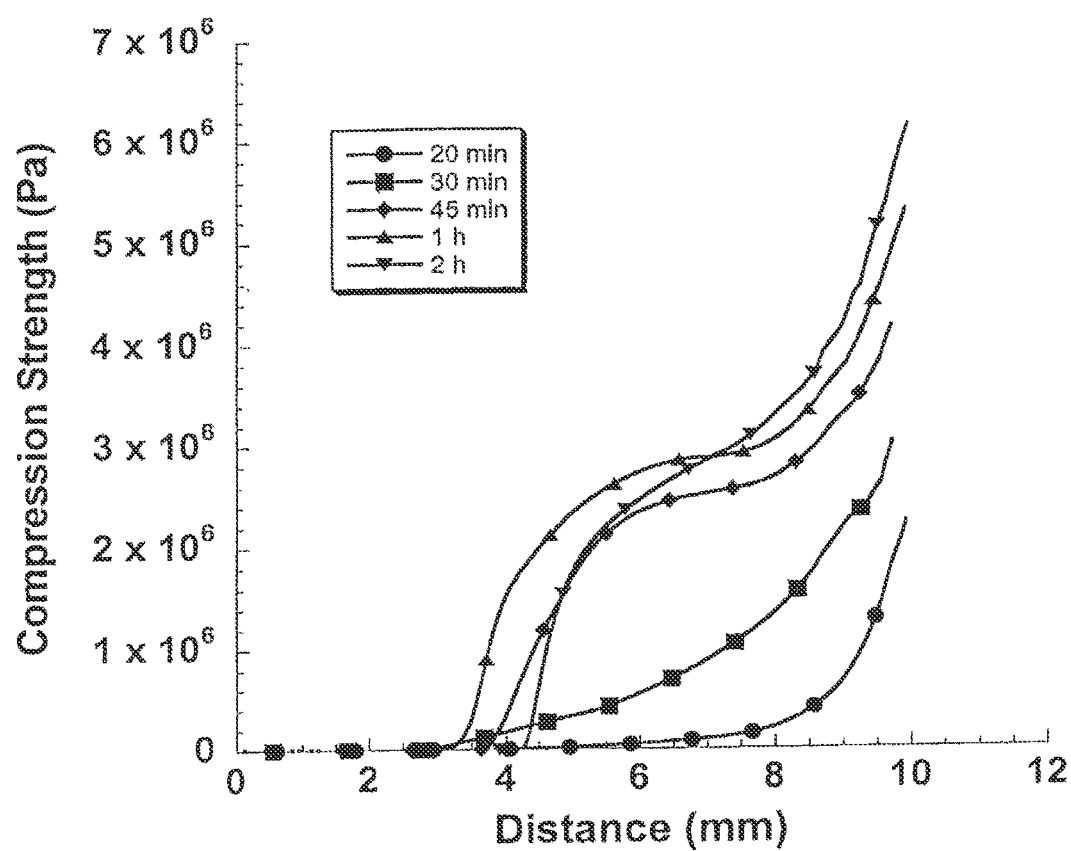
FIG. 4C. Compression strength (Pa) versus distance (mm) at various times and after being heated to 70° C. for 1 hour and then allowed to cool in room temperature for composites with PCL/tocopherol/microsized HA (29 wt % HA).
Figure 5:
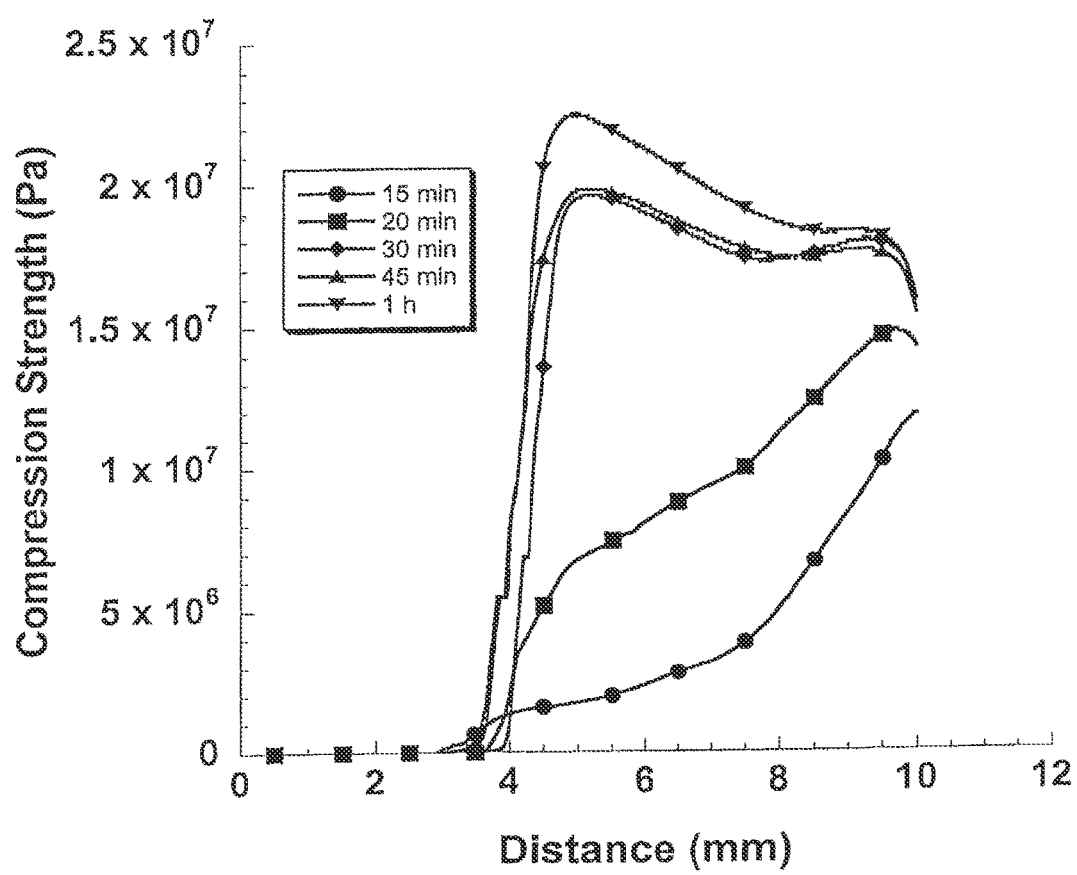
FIG. 5. Compression strength (Pa) versus distance (mm) at various times for PCL/PEG20000/nanosized HA (31 wt % HA) after being heated to 70° C. for 1 hour and then allowed to cool in room temperature.

The compression strength measurements for PCL/tocopherol/HA composites (see Example 3) with nanosized HA in the presence of amino acids are shown in FIG. 4a and in Table 2. The HA nanoparticles were produced according to Example 2. For this composite, the compressive strength stayed below 4 MPa for 45 minutes, allowing facile moldability during this period of time. After 60 minutes, this composite reached a plateau in compressive strength, with a maximum compressive strength of 7.3 MPa.

For PCL/tocopherol/HA composites (see Example 3) with nanosized HA particles without amino acids prepared according to Example 1, the shapeability was maintained up to approximately 45 minutes with the compressive strength staying below 4 MPa (see FIG. 4b). Maximum compressive strength was reached after 6 h. Substituting nanosized HA with microsized HA gave slightly lower compression strengths, as seen in FIG. 4c and Table 2. Surprisingly, the presence of tocopherol as a plasticizer effectively retards the aggregation of polymer chains, thereby enabling facile shapeability for a longer period of time. Thus, the invention includes methods of decreasing hardening speed of the composite by adding more plasticizer.

A composite with poly(DL-Lactide)/eugenol/HA was prepared according to Example 4. Due to the high solubility of poly(DL-Lactide) in eugenol, this composite was a viscous paste which did not harden even after prolonged storage.

Mixture of Plasticizers

Figure 6:
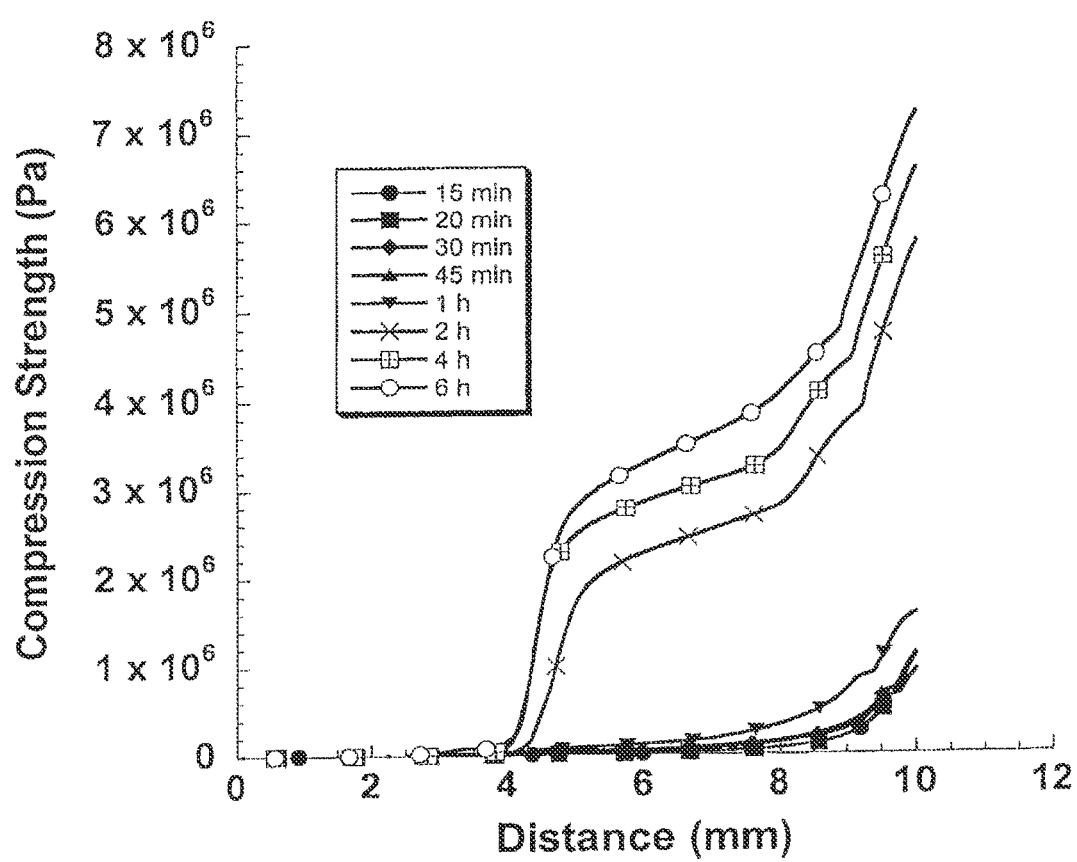
FIG. 6. Graph of compression strength (Pa) versus distance (mm) at various times for PCL/tocopherol/eugenol/nanosized HA (29 wt % HA), after being heated to 70° C. for 1 hour and then allowed to cool in room temperature.
Figure 7A:
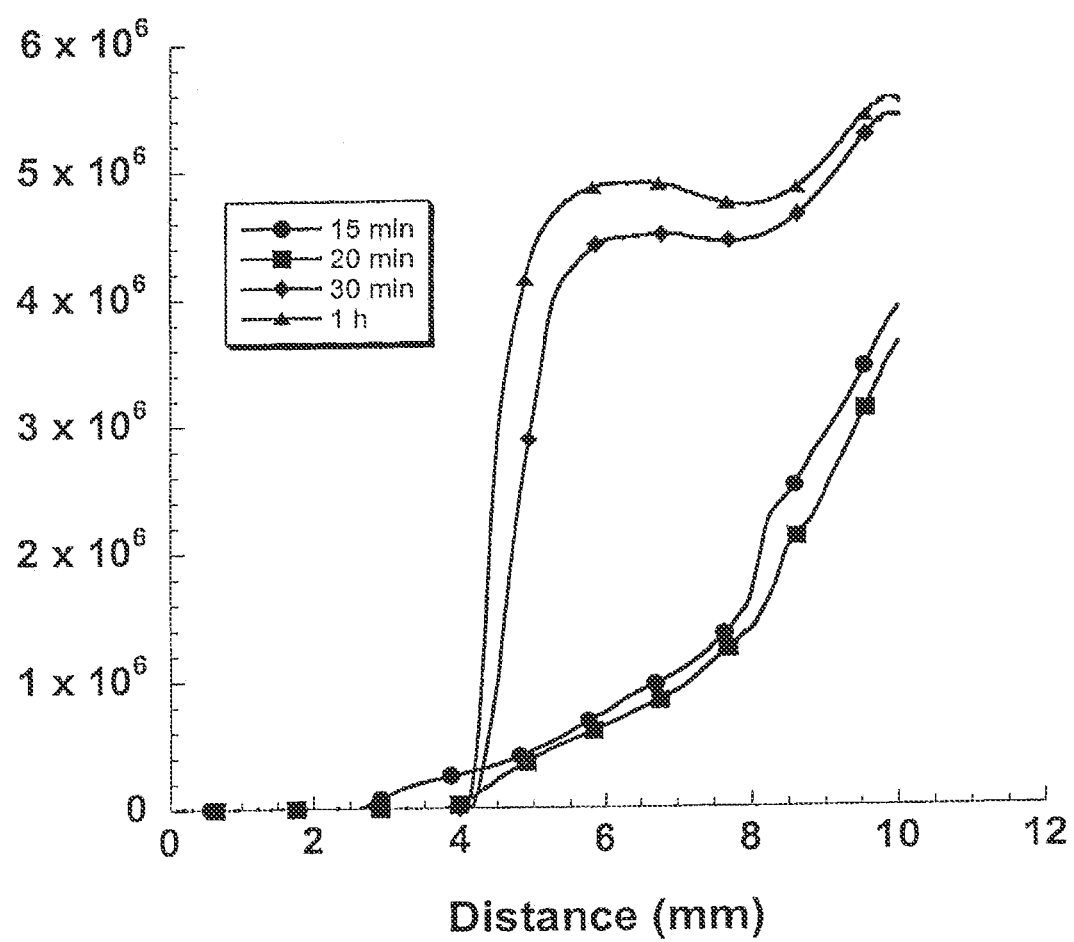
FIG. 7A. Compression strength (MPa) versus distance (mm) for composites with PCL/tocopherol/Monoolein/nanosized HA (31 wt % HA) after being heated to 70° C. for 1 hour and then allowed to cool in room temperature.
Figure 7B:
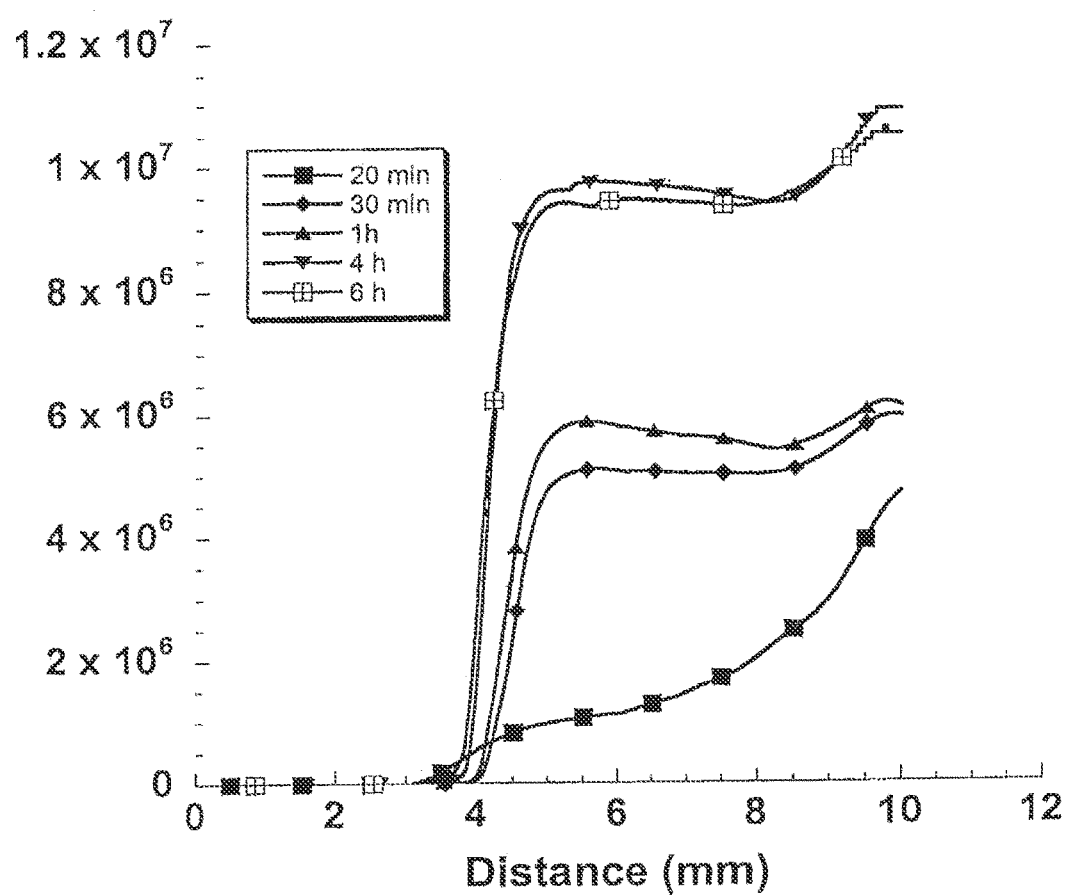
FIG. 7B. Compression strength (MPa) versus distance (mm) for composites with PCL/tocopherol/Monoolein/nanosized HA (38 wt % HA) after being heated to 70° C. for 1 hour and then allowed to cool in room temperature.

A mixture of two plasticizers can also be employed in order to retard the aggregation process even further. Eugenol, a biologically compatible lipophilic compound, was added to the PCL/tocopherol/HA system. Eugenol is a better solvent for PCL than tocopherol and has a stronger influence on the polymer aggregation process. The hardening speed can also be controlled by the type of plasticizer. Using equal amounts of tocopherol and eugenol (see Example 7) effectively inhibited polymer chain aggregation and made it possible to readily shape the composite for up to 120 minutes at room temperature. This can be compared with a composite with only tocopherol as plasticizer, which enabled facile shapeability. The results from these measurements are shown in FIG. 6 and Table 3. As seen in Table 3, the final strength of the PCL/tocopherol/eugenol/HA composite was around 6.7 MPa, i.e. in the same range as for PCL/tocopherol/HA. The invention includes methods of decreasing the hardening speed of the composite by increasing the ratio of eugenol to tocopherol.

A poly(DL-Lactide)/eugenol/tocopherol/HA composite was prepared according to Example 5. After heating and cooling to room temperature, this composite was possible to shape by hand for 30 minutes. It then solidified to an elastic, rubber-like substance.

Mixture of Polymers

A poly(DL-Lactide)/PCL/eugenol/tocopherol/HA composite was prepared according to Example 6. After heating and cooling, this composite was possible to shape by hand for 120 minutes.

Compression Strength of Porous Composites

As previously described, bioresorbable plasticizers, such as lipophilic and amphiphilic molecules, are successfully used to inhibit the rapid aggregation of polymer chains and thus increase the period of time during which the composite can be freely formed. After implantation of the composite in the body, the plasticizers are resorbed by the human body, leaving a porous structure consisting of nanocrystalline HA and polymer, suitable for bone cell growth in a vertebrate animal. The invention includes methods of inducing bone growth in a bone defect by applying an effective amount of the composite at the site of the bone defect. After the scaffold is implanted in the body, the body resorbs the plasticizers, and bone growth occurs.

Figure 8:
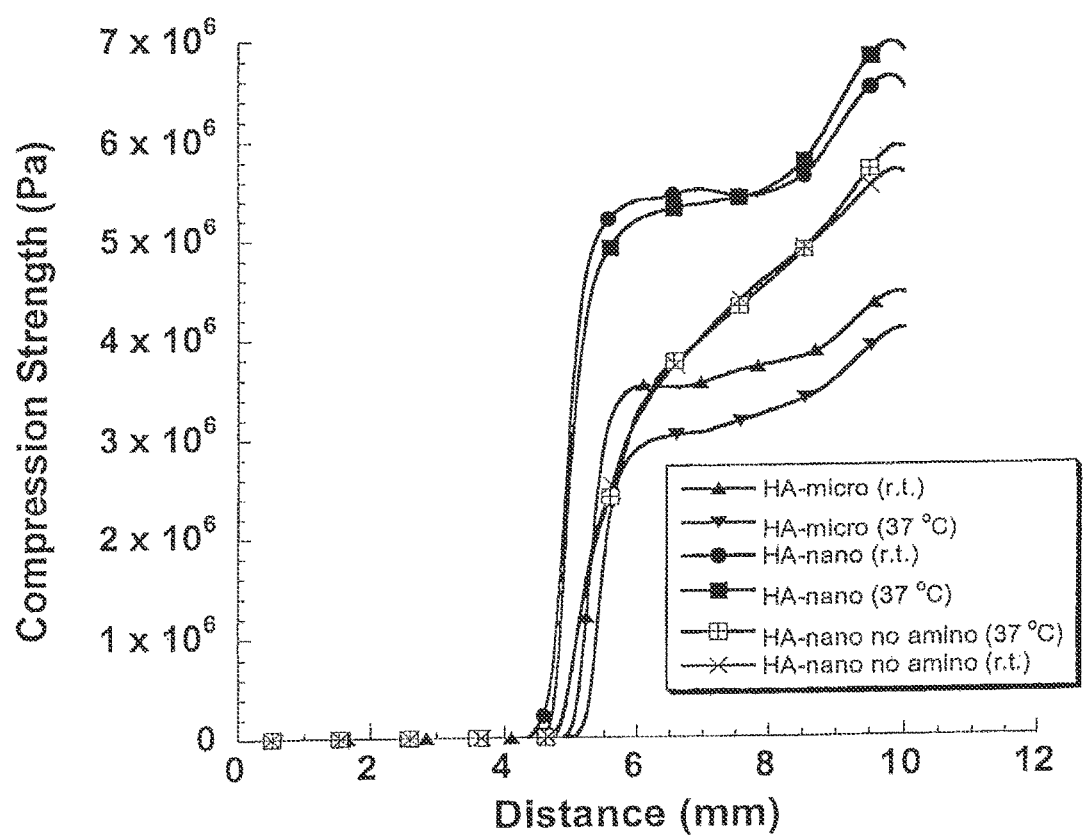
FIG. 8. Compression strength (MPa) versus distance (mm) for ethanol extracted composites measured at both room (r.t.) and body temperature for PCL/tocopherol/nanosized HA (29 wt % HA), PCL/tocopherol/microsized HA (29 wt % HA) and PCL/tocopherol/nanosized HA without amino acids (29 wt % HA).
Figure 9:
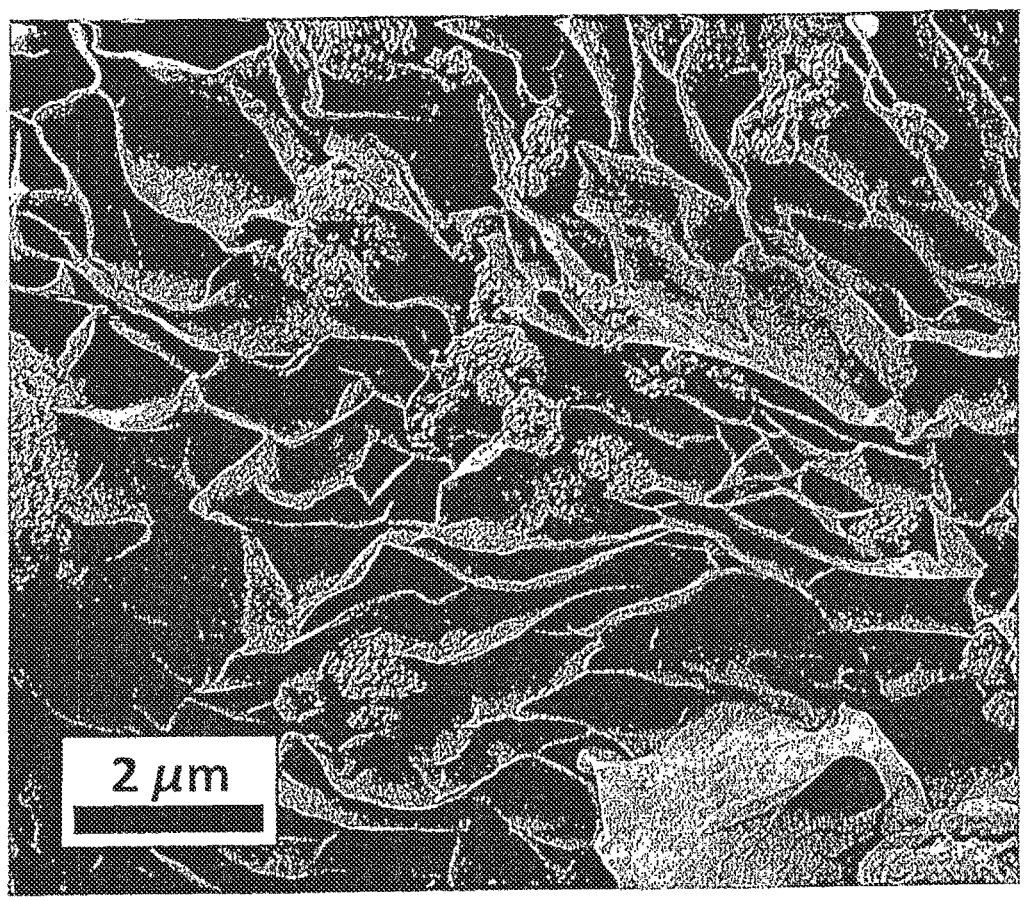
FIG. 9. SEM image of a PCL/tocopherol/nanosized HA composite after removal of tocopherol via extraction with ethanol (magnification 30 kx).

In order to mimic the resorption process, the plasticizer was extracted using ethanol (see Example 11) rendering a porous composite (see FIG. 9). Subsequently, compression strength measurements were performed on the obtained porous samples in order to compare the strength after the removal of the plasticizer. This was done for composites with nanosized HA, with and without attached amino acids, and microsized HA. The results of the measurements are shown in FIG. 8 and Table 4. As seen from this table, the compression strength of a composite with nanosized HA was around 6.5 MPa, compared to the composite with microsized HA, which had a strength of 4.0 MPa. Thus, the nanosized HA creates a composite with 70% higher strength than when using microsized HA. As also can be seen from Table 4 and FIG. 8, the extracted composite containing HA without amino acids displayed composite strengths in between that shown by composites containing nanocrystalline and microsized HA. At room temperature the compression strength was measured to 5.7 MPa. At body temperature a slight increase was observed (5.9 MPa). Hence, use of nanocrystalline HA results in a composite with 45% higher compressive strength compared to employing microsized HA. In summary, the use of nanocrystalline HA either in the presence or in the absence of amino acids renders a composite with high compressive strength, which is not affected by a rise in temperature. The compressive strength displayed at room temperature is not decreased at body temperature. This can be compared to the use of microsized HA where a lower compressive strength is observed at body temperature.

Figure 10A:
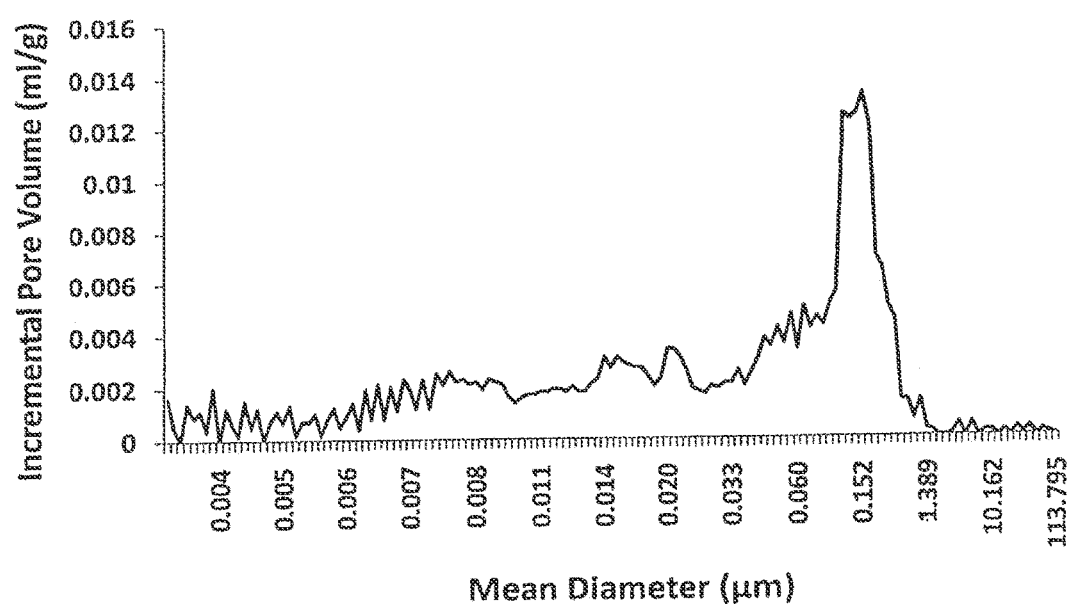
FIG. 10A. Pore size distributions for PCL/tocopherol/nanosized HA composite, obtained with mercury porosimetry measurements.
Figure 10B:
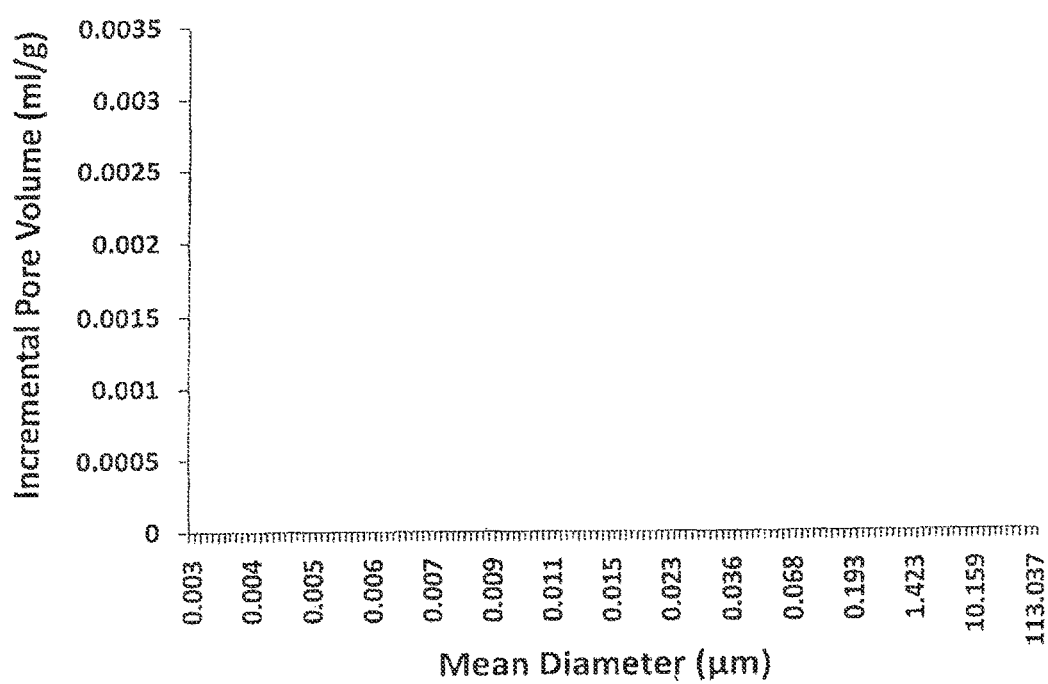
FIG. 10B. Pore size distributions for PCL/tocopherol/Monoolein/nanosized HA composite, obtained with mercury porosimetry measurements.

A SEM image of a composite with the plasticizer extracted is shown in FIG. 9 (for procedure, see Example 12). Mercury porosimetry measurements (see Example 13) revealed that after extraction of the tocopherol, the PCL/tocopherol/HA composite generated pores in the size range of roughly 0.1-1 μm (see FIG. 10a). Employing a mixture of equal amounts of tocopherol and monoolein as plasticizers (see Example 8) resulted in pores with small pore volumes in the size range of approximately 0.01-0.1 μm as well as larger pores in the 10 μm region (see FIG. 10b). The overall porosity (ratio of the volume of pores to the total volume, including the solid and void components) was 31% and 14% for PCL/tocopherol/HA and PCL/tocopherol/Monoolein/HA, respectively. After resorption, the absence of plasticizer renders a composite with mechanical strength similar to that observed for a pure polymer/HA composite. Combining tocopherol with the amphiphilic substance monoolein renders composites, which are freely moldable for approximately 30 minutes. Increasing the amount of HA from 31 to 38 wt % increases the strength of the composite as well as affecting the time before complete hardening (see FIG. 7 and Table 3). Conclusively, amphiphilic substances such as monoolein can be used to control the porosity of the implanted bone scaffold material. The porosity can be adjusted by altering the ratio of tocopherol to monoolein. Increasing the amount of monoolein decreases the porosity. The compression strength can be increased by increasing the percentage of nanosized HA. As can be seen in Table 3, composites comprising approximately 29-38% by weight of nanosized HA were found to be of suitable strength.

PCL/PEG/HA

As previously mentioned, U.S. Pat. No. 7,186,759 describes a moldable composite based on a three component system consisting of a biodegradable polymer, a water-soluble or hydrolytically degrading polymer, such as poly (ethylene glycol) and a bioactive substance, such as HA. The task assigned to poly(ethylene glycol) is the ability to induce porosity upon hydrolysis. Preparing a composite composed of PCL, polyethylene glycol (PEG20000) and nanocrystalline HA (see Example 10), resulted in a shapeable composite with a final mechanical strength comparable with pure PCL. However, the moldability was restricted to a short period of time, approximately 15 minutes, after which the compression strength levelled out at around 15.5 MPa (see FIG. 5 and Table 2). It can also be seen from Table 2 that around the human body temperature, 37° C., the PCL/PEG/HA composite was impossible to shape by hand. This indicates that poly(ethylene glycol) acts like a hardening agent, which accelerates the hardening process, rather than the opposite effect of that displayed by tocopherol when present in a polymer matrix.

Chemicals Used

The biodegradable polymers poly(caprolactone) and poly (D,L-lactide) were obtained from Sigma Aldrich, Sweden and Polysciences, USA, respectively (see Examples 3-9).

The plasticizers tocopherol, eugenol, monoolein and 1,2,3-triacetoxypropane were all obtained from Sigma Aldrich, Sweden. Similarly, all reagents, such as calcium oxide, L-aspartic acid and L-lysine used in the synthesis of HA nanoparticles were acquired from Sigma Aldrich, Sweden (see Examples 1-10). Phosphoric acid (85 wt %) was obtained from Fluka.

Poly(ethylene glycol) 20000 used in Example 10 was obtained from Fluka.

The commercial HA with a specific surface area of 9.4 m$^2$/g used in the preparation of composites was obtained from Sigma Aldrich, Sweden.

The features of the present invention will be more clearly understood by reference to the following examples, which are not to be construed as limiting the invention.

EXAMPLES

As was described in U.S. Patent Application No. 60/996,561, the disclosure of which is hereby incorporated by reference, the following examples of the synthesis procedures of mouldable composites, in conjunction with the general and detailed descriptions herein, more fully illustrate the nature and character of the present invention.

Example 1

Synthesis of Nanocrystalline Hydroxyapatite Gel 2.82 g of CaO was mixed with 150 ml of $H_2O$ in a beaker. The dispersion was allowed to stir for 1 hour. In a separate beaker, 3.45 g of $H_3PO_4$ (85 wt %) was mixed with 150 ml of $H_2O$. The contents in the two beakers were mixed at ambient temperature, and the resulting gel was allowed to stir for 12 hours. The mixture was filtered in a grade 4 glass filter and washed extensively with water (2.5 L). A portion of the gel was dried and analyzed with XRD and nitrogen adsorption. The specific surface area, as calculated with the BET method, of this sample was found to be 200 $m^2/g$.

Example 2

Synthesis of Nanocrystalline Hydroxyapatite Gel with Amino Acids

The nanocrystalline hydroxyapatite was prepared as follows. 6.70 g of L-Aspartic acid was mixed with 150 ml $H_2O$ in a beaker. 2.82 g of CaO was added to this solution, and the mixture was allowed to stir for 1 hour. In a separate beaker, 3.45 g $H_3PO_4$ (85 wt %), 6.65 g L-Lysine and 150 ml $H_2O$ was mixed. The pH of this solution was 6.46. The contents in the two beakers were mixed at ambient temperature, and the pH was measured to 8.10. The mixture was allowed to stir for 12 hours. The mixture was filtered in a grade 4 glass filter and washed extensively with water (2.5 L) to remove excess amino acids. The pH of the resulting gel was measured to 7.90.

A portion of the gel was dried and analyzed with XRD and nitrogen adsorption. The X-ray diffractogram is shown in FIG. 1. The specific surface area, as calculated with the BET method, of this sample was found to be 210 $m^2/g$.

Example 3

PCL/Tocopherol/HA

HA gel was prepared according to Example 1 or 2. The gel, consisting of coated hydroxyapatite particles and water, was mixed with 6 grams of poly(caprolactone) with a molecular weight of 80000 g/mol, and 6 grams of tocopherol. The mixture was heated to 70° C. under extensive stirring until complete evaporation of the water had occurred. The yellow colored mixture was removed from the stirring equipment and allowed to cool to room temperature. The composite was readily moldable for approximately 45 minutes, during which the compressive strength was found to be below 4 MPa. The maximum compressive strength of 6.7 MPa was reached after roughly 120 minutes.

Example 4

Poly(D,L-lactide)/Eugenol/HA a) Synthesis of Nanocrystalline Hydroxyapatite Gel
Prepared as previously described in Example 1 or 2.
b) Production of Mouldable Bone Substitute
The resulting gel, consisting of coated hydroxyapatite particles and water, was mixed with 4 grams of eugenol. The mixture was heated to 70° C. under extensive stirring until complete evaporation of the water had occurred. The paste-like blend was subsequently added to 4 grams of poly(D,L-lactide) dissolved in 4 grams of eugenol. The mixture was then once again heated to 70° C. and stirred until a homogeneous dough-like mixture was obtained. The resulting yellow coloured composite material was removed from the stirring equipment and allowed to cool to room temperature.

Example 5

D,L-Lactide/Tocopherol/Eugenol/HA a) Synthesis of Nanocrystalline Hydroxyapatite Gel
Prepared as previously described in Example 1 or 2.
b) Production of Moldable Bone Substitute
The resulting gel, consisting of coated hydroxyapatite particles and water, was mixed with 3 grams of tocopherol. The mixture was heated to 70° C. and stirred until a dry and brown colored powder was obtained. In a separate beaker, 3 grams of D,L-lactide was mixed with 3 grams of eugenol followed by heating to 70° C. for approximately 3 h or until a homogenous blend was observed. To the homogenous melt, tocopherol/HA powder was added and the mixture was subsequently kept stirred at 70° C. Gradually, the temperature was increased to 90° C. in order to facilitate blending of the powder with the viscous polymer/oil melt. The temperature was maintained at 90° C. until a homogeneous material was attained, after which the material was removed from the stirring equipment. The reaction mixture was allowed to cool to room temperature, resulting in a paste-like material.

Example 6

PCL/Poly(D,L-Lactide)/Tocopherol/Eugenol/HA a) Synthesis of Nano Crystalline Hydroxyapatite Gel
Prepared as previously described in Example 1 or 2.
b) Production of Moldable Bone Substitute
Nanocrystalline hydroxyapatite gel was added to 1.5 grams of tocopherol of and 1.5 grams of eugenol. The reaction mixture was heated to 70° C. and stirred until a dry and brown colored powder was obtained. Prior to the addition of the tocopherol/eugenol/HA powder, 4.5 grams of poly(caprolactone) and 1.5 grams of poly(D,L-lactide) were mixed with 1.5 grams of tocopherol and 1.5 grams of eugenol. The viscous mixture was heated to 70° C. for approximately 3 h or until a homogenous blend was observed. To the homogenous melt, tocopherol/eugenol/HA powder was added and the mixture was subsequently stirred and at 70° C. until a homogenous composite material was obtained. The resulting brown coloured composite material was removed from the stirring equipment and allowed to cool to room temperature.

Example 7

PCL/Tocopherol/Eugenol/HA a.) Synthesis of Nanocrystalline Hydroxyapatite Gel
Prepared as previously described in Example 1 or 2.
b) Production of Moldable Bone Substitute
Prior to the addition of nanocrystalline hydroxyapatite gel, 3 grams of eugenol was mixed with 3 grams of tocopherol and 6 grams of poly(caprolactone) with a molecular weight of 80000 g/mol. The viscous mixture was heated to 70° C. for approximately 2 hours without stirring followed by 2 hours with stirring. To the homogenous and yellow melt, hydroxyapatite, as a gel, was added. The mixture was then heated to 70° C. under extensive stirring until complete evaporation of the water had occurred. The resulting brown colored composite material was removed from the stirring equipment and allowed to cool to room temperature. The combination of tocopherol/eugenol as plasticizer enables the composite to be shapeable for up to 120 minutes. The final compressive strength of the PCL/tocopherol/eugenol/HA composite was around 6.7 MPa.

Example 8

PCL/Tocopherol/Monoolein/HA a) Synthesis of Nanocrystalline Hydroxyapatite Gel
Prepared as previously described in Example 1 or 2.
b) Production of Moldable Bone Substitute
Prior to the addition of nanocrystalline hydroxyapatite gel, 3 grams of monoolein was mixed with 3 grams of tocopherol and 5 grams of poly(caprolactone) with a molecular weight of 80000 g/mol. The viscous mixture was heated to 70° C. for approximately 12 hours before the hydroxyapatite gel was added. The mixture was subsequently heated to 70° C. under extensive stirring until complete evaporation of the water had occurred. The resulting yellow colored composite material was removed from the stirring equipment and allowed to cool to room temperature. The combination of tocopherol/monoolein as plasticizer renders composites, which are freely moldable for approximately 30 minutes after, and which reach a maximum compression strength of approximately 5.5 MPa.

Example 9

PCL/Monoolein/Triacetin/HA a) Synthesis of Nanocrystalline Hydroxyapatite Gel
Prepared as previously described in Example 1 or 2.
b) Production of Moldable Bone Substitute
Prior to the addition of nanocrystalline hydroxyapatite gel, 3 grams of monoolein was mixed with 3 grams of 1,2,3-triacetoxypropane and 6 grams of poly(caprolactone) with a molecular weight of 80000 g/mol. The viscous mixture was heated to 70° C. To the homogenous and slightly opaque melt, hydroxyapatite, as a gel, was added. The mixture was subsequently heated to 70° C. under extensive stirring until complete evaporation of the water had occurred. The obtained off-white composite material was removed from the stirring equipment and allowed to cool to room temperature. The combination of monoolein and 1,2,3-triacetoxypropane as plasticizer results in composites, which are freely moldable for approximately 45 minutes, and with a compression strength of 6.3 MPa, similar to that of PCL/tocopherol/HA composites (see Example 3).

Example 10

PCL/PEG20000/HA

To evaluate the effect of adding a hydrolyzable compound acting as a porogen in combination with a biodegradable polymer and nanosized HA of the invention herein, the mechanical properties and molding times for the composite prepared in U.S. Pat. No. 7,186,759 was compared with a composite described in the invention herein. The composite in U.S. Pat. No. 7,186,759 was prepared as described, however, using nanocrystalline HA particles instead of micrometer sized HA (see description below).

a) Synthesis of Nanocrystalline Hydroxyapatite Gel
Prepared as previously described in Example 1 or 2.
b) Production of Moldable Bone Substitute
Prior to the addition of nanocrystalline hydroxyapatite gel, 5 grams of PEG 20000 was mixed with 6.7 grams of poly(caprolactone) at 80° C. for 2 h followed by mechanical stirring at the same temperature. The mixture was then kept at 80° C. under extensive stirring until complete evaporation of the water had occurred. The resulting opaque composite material was removed from the stirring equipment and allowed to cool to room temperature. The composite reached a maximum compressive strength of approximately 15 MPa after approximately 20-30 minutes.

Example 11

Extraction of Plasticizer

The extraction process took place over a period of 6 days at room temperature with exchange of the ethanolic phase every second day. The compression strength was measured at room temperature and at 37° C., as can be seen from Table 4. For experiments performed at body temperature, the composite material was heated to 37° C. for at least one hour prior to measurement. The compression strength values shown in Table 4 represent an average over at least four experiments.

Example 12

Preparation of Ethanol Extracted Composite Samples for SEM-analysis

Extracted samples were prepared according to the method described in Example 11. Extracted specimens were placed on carbon tape and subsequently sputtered with a thin gold film using a JEOL sputter coater. SEM analysis was performed on a LEO Ultra 55 FEG SEM equipped with an Oxford Inca EDX system, operating at 2-5 kV. A secondary electron detector was used for detection.

Example 13

Preparation of Samples for Hg-porosimetry Measurements

Samples were molded by hand into cubes with the dimensions of approximately 1×1×1 cm. The tocopherol phase was subsequently extracted with ethanol according to the procedure previously described. Prior to analysis, the samples were placed under vacuum at ambient temperature overnight.

Example 14

Preparation of Samples for TEM Analysis

Specimens were prepared by grinding the HA material into a fine powder, dispersing the powder in ethanol and then placing a few drops of the dispersion onto a holey carbon grid followed by drying at room temperature. The analysis was performed on a JEOL 1200 EX II microscope operating at 120 KV.

The invention in its broader aspects is not limited to the specific details shown and described and departures may be made from such details without departing from the principles of the invention and without sacrificing its chief advantages.

REFERENCES

1. H. A. Lowenstam and S. Weiner, *On biomineralization*, Oxford University Press, New York, 1989.
2. L. Lidgren and M. Nilsson, 2004.
3. U. Ripamonti, *Journal of bone and joint surgery-American Volume*, 1991, 73A, 692-703.
4. L. Nair and C. Laurencin, *Progress in polymer science*, 2007, 32, 762-798.
5. M. C. Azevedo, R. L. Reis, M. B. Claase, D. W. Grijpma and J. Feijen, *J. Mater. Sci.: Mat. Med.*, 2003, 14, 103-107.
6. J.-J. Sun, C.-J. Bae, Y.-H. Koh, H.-E. Kim and H.-W. Kim, *J. Mater. Sci.: Mat. Med.*, 2007, 18.
7. H. Niiranen, T. Pyhalto, O. Rokkanen, M. Kellomaki and P. Tormala, *J. Biomed. Mater. Res. A*, 2004, 69A, 699-708.
8. M. Wang, *Biomaterials*, 2003, 24, 2133-2151.
9. C. Agrawal and R. Ray, *J. Biomed Mat. Res.*, 2001, 55, 141-150.
10. R. C. Thomson, M. J. Yaszemski, J. M. Powers and A. G. Mikos, *Biomaterials*, 1998, 19, 1935-1943.
11. J. DeGroot, H. Kuijper and A. Pennings, *J. Mater. Sci.: Mat. Med.*, 1997, 8, 707-712.
12. S. Lee, B. Kim, S. Kim, S. Choi, S. Jeong, I. Kwon, S. Kang, J. Nikolovski, D. Mooney, Y. Han and Y. Kim, *J. Biomed. Mater. Res. A*, 2003, 66A, 29-37.
13. K. G. Marra, L. E. Weiss, J. W. Calvert and P. N. Kumta, Carnegie Mellon University, USA, 2000.
14. X. Guo, J. E. Gough, P. Xiao, J. Liu and Z. Shen, *J. Biomed Mater. Res. A*, 2007, 82A, 1022-1032.
15. L. Meirelles, A. Arvidsson, M. Andersson, P. Kjellin, T. Albrektsson and A. Wennerberg, *J. Biomed. Mater. Res. A*, 2007, 10.1002/jbm.a.31744.
16. J. Wei, Y. Li and K. Lau, *Composites part B: engineering*, 2007, 38, 301-305.
17. H. Ramay and M. Zhang, *Biomaterials*, 2003, 24, 3293-3302.
18. J. S. Temenoff and A. G. Mikos, *Biomaterials*, 2000, 21, 2405-2412.
19. A. A. Deschamps, A. A. v. Apeldoorn, H. Hayen, J. D. d. Bruijn, U. Karst, D. W. Grijpma and J. Feijen, *Biomaterials*, 2004, 25, 247-258.

TABLE 1

| | PCL | | PCL/HA (29 wt % nanosized HA)[a] | | PCL/HA (29 wt % microsized HA)[b] | |
|---|---|---|---|---|---|---|
| Time (min) | Temp. (° C.) | Compression strength (MPa) | Temp. (° C.) | Compression strength (MPa) | Temp. (° C.) | Compression strength (MPa) |
| 0 | 70.0 | — | 70.5 | — | 70.0 | — |
| 10 | 48.5 | — | 49.0 | — | 47.5 | — |
| 15 | 41.5 | 5.65 | 41.5 | 11.9 | 40.5 | 11.0 |
| 20 | 39.5 | 9.65 | 40.0 | 15.6 | 40.0 | 10.8 |
| 30 | 31.5 | 14.8 | 31.0 | 16.9 | 32.0 | 14.9 |
| 45 | 25.5 | 15.7 | 26.5 | 15.2 | 27.0 | 13.3 |
| 60 | 23.5 | 14.1 | 25.0 | 16.5 | 24.5 | 14.1 |
| 120 | 22.5 | 13.2 | 24.0 | 15.8 | 23.0 | 13.8 |
| 240 | 22.0 | 14.8 | 24.0 | 16.1 | 23.0 | 13.5 |
| 360 | 22.0 | 15.1 | 24.0 | 16.6 | 23.0 | 15.6 |
| 1440 | 22.0 | 15.0 | 22.0 | 17.2 | 22.0 | 14.5 |

[a]The nanosized HA was prepared according to Example 2.
[b]The microsized HA was purchased from Sigma Aldrich. The specific surface area was determined to 18 m$^2$/g.

TABLE 2

| | PCL/TOC/HA (29 wt % nanosized HA)[a] | | PCL/TOC/HA (29 wt % microsized HA)[b] | | PCL/PEG/HA (31 wt % nanosized HA)[c] | | PCL/TOC/HA (29 wt % nanosized HA, without amino acids)[d] | |
|---|---|---|---|---|---|---|---|---|
| Time (min) | Temp. (° C.) | Compression strength (MPa) | Temp. (° C.) | Compression strength (MPa) | Temp. (° C.) | Compression strength (MPa) | Temp. (° C.) | Compression strength (MPa) |
| 0 | 69.5 | — | 69.0 | — | 70.5 | — | 72.5 | — |
| 10 | 43.5 | — | 47.0 | — | 47.5 | — | 52 | — |
| 15 | 37.0 | 2.60 | 40.5 | — | 42.0 | 11.8 | 46 | — |
| 20 | 34.5 | 1.89 | 35.0 | 2.21 | 41.0 | 42.0 | 40 | — |
| 30 | 30.5 | 3.14 | 30.5 | 3.03 | 32.0 | 15.9 | 32 | 2.79 |
| 45 | 27.5 | 5.39 | 26.0 | 4.13 | 27.5 | 15.4 | 32 | 3.56 |
| 60 | 25.0 | 6.40 | 24.0 | 5.23 | 25.0 | 15.8 | 25.5 | 5.01 |
| 120 | 23.5 | 6.75 | 23.0 | 6.13 | 22.5 | 14.9 | 23.5 | 4.68 |
| 240 | 23.5 | 6.27 | 23.0 | 6.47 | 22.5 | 15.5 | 22 | 4.91 |
| 360 | 23.5 | 7.32 | 23.0 | 6.32 | 23.0 | 15.1 | 23 | 4.62 |
| 1440 | 22.0 | 6.65 | 22.0 | 6.24 | 22.0 | 15.6 | 22 | 5.45 |

[a]The HA used was prepared according to Example 2.
[b]The HA used was purchased from Sigma Aldrich. The specific surface area was determined to 18 m$^2$/g
[c]PEG20000 was used.
[d]The HA used was prepared according to Example 1.

TABLE 3

| | PCL/TOC/Eugenol/HA (29 wt % nanosized HA)[a] | | PCL/TOC/MO/HA (31 wt % nanosized HA)[a] | | PCL/TOC/MO/HA (38 wt % nanosized HA)[a] | |
|---|---|---|---|---|---|---|
| Time (min) | Temp (° C.) | Compression strength (MPa) | Temp (° C.) | Compression strength (MPa) | Temp (° C.) | Compression strength (MPa) |
| 0 | 69.0 | — | 70 | — | 70.0 | — |
| 10 | 50.0 | — | 47.5 | — | 45.0 | — |
| 15 | 43.5 | 0.92 | 41 | 3.91 | 39.0 | — |
| 20 | 36.5 | 0.94 | 37 | 3.63 | 36.5 | 4.71 |
| 30 | 30.0 | 1.12 | 31 | 5.40 | 31.0 | 5.95 |
| 45 | 26.0 | 1.10 | — | — | 26.5 | 6.12 |
| 60 | 24.5 | 1.57 | 24.5 | 5.52 | 24.5 | 6.11 |
| 120 | 23.0 | 5.75 | 22.5 | 5.64 | 23.5 | 6.09 |
| 240 | 22.0 | 6.58 | 22.5 | 5.41 | 23.5 | 10.9 |
| 360 | 21.5 | 7.21 | 22.5 | 5.55 | 24.5 | 10.5 |
| 1440 | 22 | 6.44 | — | — | 22 | 9.6 |

[a]The HA used was prepared according to Example 2.

TABLE 4

| Temperature (° C.) | PCL/HA (29 wt % nanosized HA, MPa)[a] | PCL/HA (29 wt % microsized HA, MPa)[b] | PCL/HA (29 wt % nanosized HA without amino acids, MPa) |
|---|---|---|---|
| Room temp. (20-22) | 6.52 | 4.45 | 5.67 |
| 37 | 6.88 | 4.09 | 5.92 |

[a]The composite was prepared by extracting PCL/TOC/HA (29 wt % nanosized HA) with EtOH (see Example 11 for further details).
[b]The composite was prepared by extracting PCL/TOC/HA (29 wt % microsized HA) with EtOH (see Example 11 for further details).

We claim:

1. A composite for producing a scaffold for bone growth comprising:
    calcium phosphate particles having a length of 10-20 nm;
    a biodegradable polymer; and
    monoolein,
    wherein the composite is shapeable by hand for at least 10 minutes after a heating step.

2. The composite of claim 1, further comprising an amphiphilic substance.

3. The composite of claim 1, wherein the scaffold is an implantable scaffold and the shapeable composite is cooled to room temperature to harden the shapeable composite to form the implantable scaffold.

4. The composite of claim 1, wherein the heating step comprises heating the composite to a temperature sufficient to form the composite that is shapeable by hand for a given period of time.

5. The composite of claim 1, wherein the scaffold comprises a biologically active factor selected from the group consisting of an antibiotic, chemotherapeutic, bone cell inducer, bone cell stimulator, tissue promoting factor, tissue decomposition inhibitor, growth factor, and any combination thereof.

6. The composite of claim 1, wherein the calcium phosphate particles are selected from tricalcium phosphate, octacalcium phosphate, tetracalcium phosphate, dicalcium phosphate, hydroxyapatite, or any combination thereof.

7. The composite of claim 1, wherein the composite further comprises 1,2,3-triacetoxypropane and poly-caprolactone.

8. A composite for producing a nanocrystalline hydroxyapatite (HA) scaffold for bone growth comprising:
    nanocrystalline HA particles having a length of 10-20 nm and a specific surface area of 200 m²/g or greater;
    a biodegradable polymer; and
    monoolein.

9. The composite of claim 8, wherein the nanocrystalline HA particles comprise an amino acid coating.

10. The composite of claim 9, wherein the amino acid coating is removed prior to combining the nanocrystalline HA particles with the biodegradable polymer and monoolein.

11. The composite of claim 9, wherein the amino acid coating comprises L-aspartic acid and L-lysine.

12. The composite of claim 8, wherein the nanocrystalline HA particles, biodegradable polymer and monoolein are combined to form the nanocrystalline HA composite, and the nanocrystalline HA composite is heated and then cooled to room temperature.

13. The composite of claim 12, wherein the composite is heated to a temperature sufficient to make the composite shapeable and the cooling is carried out to harden the shapeable composite to an implantable scaffold.

14. The composite of claim 8, further comprising an amphiphilic substance.

15. The composite of claim 8, wherein the scaffold comprises a biologically active factor selected from the group consisting of an antibiotic, chemotherapeutic, bone cell inducer, bone cell stimulator, tissue promoting factor, tissue decomposition inhibitor, growth factor, and any combination thereof.

16. The composite of claim 8, wherein the scaffold further comprises tricalcium phosphate, octacalcium phosphate, tetracalcium phosphate, dicalcium phosphate, or any combination thereof.

17. The composite of claim 8, wherein the composite further comprises 1,2,3-triacetoxypropane and poly-caprolactone.

18. A nanocrystalline hydroxyapatite (HA) scaffold for bone growth comprising:
    a plurality of nanocrystalline HA particles;
    monoolein;
    1,2,3-triacetoxypropane; and
    poly-caprolactone,
    wherein nanocrystalline HA particles having a length of 10-20 nm, 1,2,3-triacetoxypropane, and poly-caprolactone are combined to form the nanocrystalline hydroxyapatite (HA) scaffold.

19. The nanocrystalline hydroxyapatite (HA) scaffold of claim 18, further comprising an amphiphilic substance.

20. The nanocrystalline hydroxyapatite (HA) scaffold of claim 18, wherein the nanocrystalline HA particles, 1,2,3-triacetoxypropane, and poly-caprolactone are combined to form a composite and the composite is heated to a temperature sufficient to form a shapeable composite.

21. The nanocrystalline hydroxyapatite (HA) scaffold of claim 20, wherein the shapeable composite is shapeable by hand for at least 10 minutes.

22. The nanocrystalline hydroxyapatite (HA) scaffold of claim 18, wherein the composite comprises a biologically active factor selected from the group consisting of an antibiotic, chemotherapeutic, bone cell inducer, bone cell stimulator, tissue promoting factor, tissue decomposition inhibitor, growth factor, and any combination thereof.

23. The composite of claim 8, wherein the composite is shapeable by hand for at least 10 minutes after a heating step.

* * * * *

UNITED STATES PATENT AND TRADEMARK OFFICE
CERTIFICATE OF CORRECTION

PATENT NO. : 9,782,435 B2
APPLICATION NO. : 14/737741
DATED : October 10, 2017
INVENTOR(S) : Kjellin et al.

Page 1 of 1

It is certified that error appears in the above-identified patent and that said Letters Patent is hereby corrected as shown below:

In the Specification

Column 2, Lines 41-42: Please correct "extrusion $^{7,}_{8}$" to read -- extrusion $^{7,8}$ --

Column 4, Line 62: Please correct "1001 kx" to read -- 100kX --

Signed and Sealed this
Twenty-fourth Day of July, 2018

Andrei Iancu
*Director of the United States Patent and Trademark Office*